United States Patent

Dolade Guardia

Patent Number: 5,860,911
Date of Patent: Jan. 19, 1999

[54] DEVICE FOR THE CONTROL OF MASCULINE INCONTINENCE

[76] Inventor: José Manuel Dolade Guardia, Castellnou 37, Barcelona, Spain, 08017

[21] Appl. No.: 992,517

[22] Filed: Dec. 17, 1997

[30] Foreign Application Priority Data

Dec. 20, 1996 [ES] Spain ..................... 9603275

[51] Int. Cl.⁶ .............. A61B 17/08; A61F 5/48
[52] U.S. Cl. ............................................. 600/39
[58] Field of Search ..................... 128/885, 886, 128/869, DIG. 15, DIG. 25; 600/38, 39, 29

[56] References Cited

U.S. PATENT DOCUMENTS

| | | | |
|---|---|---|---|
| 3,155,096 | 11/1964 | Outwin | 128/DIG. 15 X |
| 3,866,611 | 2/1975 | Baumrucker | 128/DIG. 15 X |
| 5,184,629 | 2/1993 | Erickson et al. | 600/29 X |

FOREIGN PATENT DOCUMENTS

WO 90/11063  10/1990  European Pat. Off. .

*Primary Examiner*—John P. Lacyk
*Assistant Examiner*—Samuel Gilbert
*Attorney, Agent, or Firm*—Darby & Darby

[57] ABSTRACT

The device includes a single laminar body constituted by a layer of spongy material covered on one of its faces by a sheet of semi-rigid synthetic material, constituting two successive curved areas separated from each other by a hinge fold and ending in individual flat flanges capable of coinciding when the device is folded, the latter having in one of its curved areas two transversely aligned indentations which start in the semi-rigid laminar covering element and which also affect the spongy layer, giving rise to individual smoothly convex areas intended to create two successive interruptions of the urinary duct.

6 Claims, 2 Drawing Sheets

DEVICE FOR THE CONTROL OF MASCULINE INCONTINENCE

DESCRIPTION

The present invention relates to a device for the control of masculine incontinence which offers considerable advantages with respect to what is already known, providing appreciable characteristics of novelty and of inventive activity.

Although different devices for the control of masculine incontinence are known at present, these normally have the drawback of excessive pressure on the penis or on certain parts thereof, so that their use is uncomfortable for the user and in addition, in many cases, the fitting and removal of the device is troublesome and also painful for the user.

The device for the control of incontinence which is the subject of the present invention is intended to provide the means for obstructing the urinary duct in a simple and easy manner by means of localized pressure concentrated on two successive points thereof, so that the pressure is especially reduced and therefore causes no trouble to the user. The device also has the advantage of its unitary construction in the form of a single piece easily coupled both for closure on the urinary duct and for its opening and subsequent removal.

The device is constituted essentially by a one-piece laminar element which has two smoothly curved areas separated by a hinge fold, the said curved areas ending in individual substantially straight flanges which are intended to coincide in the closing operation. The laminar element constituting the device will be formed essentially by means of a thin layer of spongy synthetic material which will bear, adhering to its outer face, preferably in the actual moulding operation, a sheet of synthetic material of semi-rigid type in order to impart a certain rigidity and elasticity to the device.

The area of the fold between the two curved parts of the device will preferably assume the shape of a U with short limbs, and along the said fold there will preferably be arranged a longitudinal cut, in order to provide the articulation with greater flexibility. The closure points intended to act on the urinary duct are formed by individual indentations of generally oval shape which, starting in the outer semi-rigid synthetic sheet, cause convexities which also affect the spongy flexible material, and which are therefore capable of acting smoothly and effectively on two successive points of the urinary duct.

The device is closed by hinging on the hinge fold of the two curved areas and surrounding the unitary assembly of the device with an outer tape capable of extending over the whole periphery of the device, fastening itself to the outer surface of the latter by means of some adhesive system such as the systems of projecting elements and small fixing hooks of known type, used for closing textile elements and the like with great ease and rapidity.

For better understanding, there are provided, by way of example, explanatory but non-limitative drawings of a device for the control of masculine incontinence produced according to the present invention.

Figure 1:
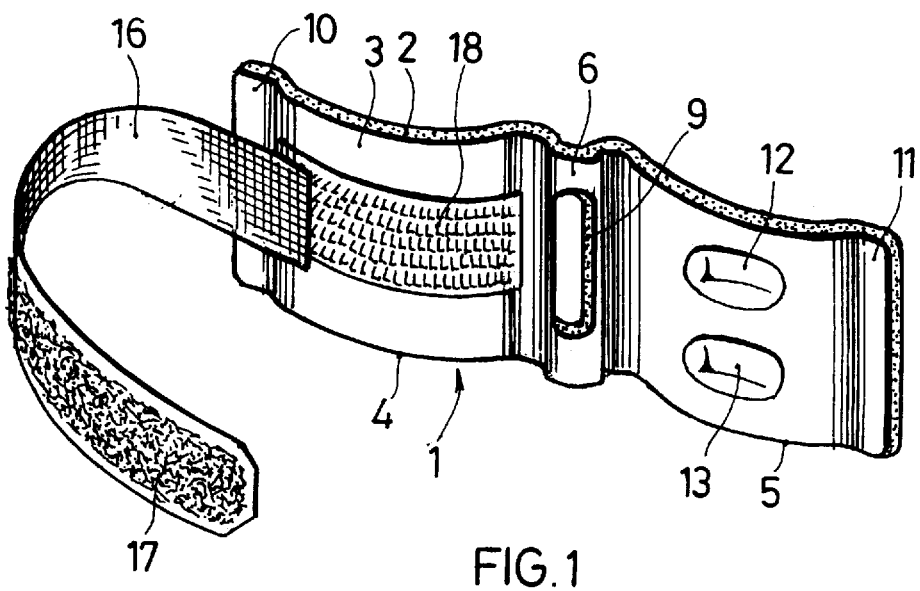
FIG. 1 is a perspective view of the device which is the subject of the present invention, completely opened out.

As can be seen in the drawings, the device for the control of incontinence which is the subject of the present invention comprises a one-piece part 1 of laminar type, which on one of its faces has a thin layer 2 of spongy material and on the other face has a sheet 3 of a semi-rigid synthetic material which imparts strength to the assembly. The device comprises two successive curved areas 4 and 5 joined by an intermediate fold 6 formed by hot stamping of the laminar element, therefore having stable characteristics. The said fold 6 will assume the shape of a U with short limbs 7 and 8, FIG. 2, permitting the articulation of the device round the aforesaid fold which, in order to improve flexibility, has a longitudinal groove 9.

The curved elements 4 and 5 have, at their ends, individual flat flanges 10 and 11 which coincide with their ends in the closed position.

Figure 2:
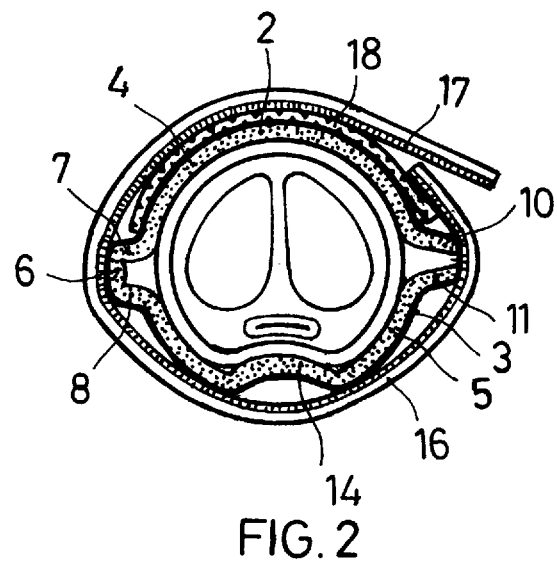
FIG. 2 shows a cross-section through the actual incontinence device when placed in position.

The urinary duct is obstructed by means of two stamped indentations 12 and 13 which start in the semi-rigid element 3, also affecting the spongy layer 2, in which they form individual convex projections, substantially oval in shape 14 and 15, aligned with each other and intended to constrict the urinary duct, as can be seen in FIG. 2 in the application of the device.

The device is closed by means of an outer tape 16 which is fixed to the periphery of the device, completely surrounding the latter, for which purpose it will have fixing means, preferably of the adhesive type, on the outer surface 3 of the device. In a preferred version, the said fixing is effected by means of a layer 18 of material fixed on the outside of the device, that is to say, on the face 3 thereof, which will coincide with and be fixed to another fastening layer 17 which the tape or band 16 has on its inner face. In a preferred version, the said tape or band 16 will have on its inner face a surface for fastening by means of a multiplicity of protuberances in the form of small rings which are capable of fixing themselves into other protuberances in the form of hook-like projecting stems of the conjoined part.

Figure 3:
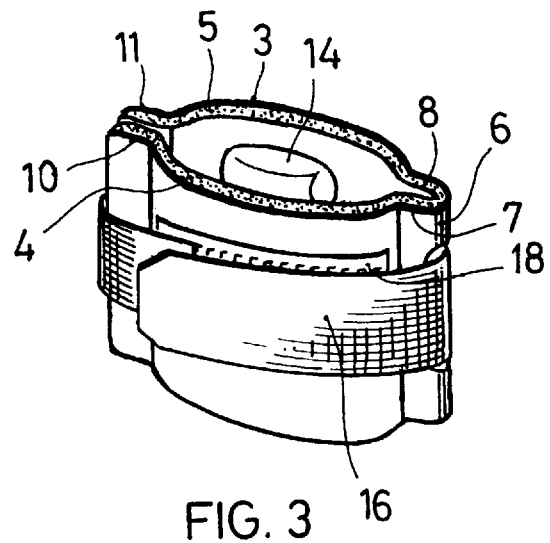
FIG. 3 is a perspective view of the device for the control of incontinence in the folded position for packaging or maintaining in the ready-for-use position.
Figure 4:
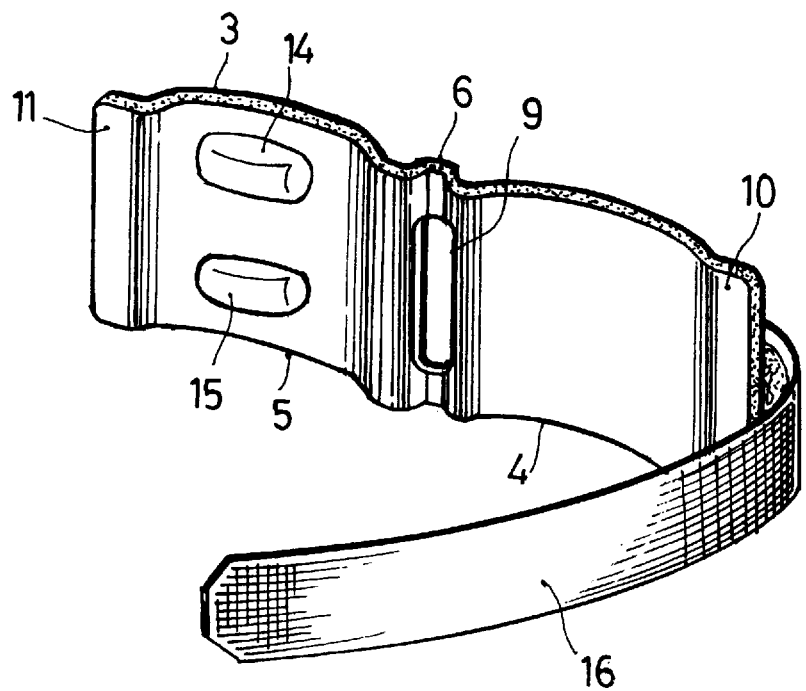
FIG. 4 is another perspective view of the device for the control of incontinence which is the subject of the present invention, showing the inner part thereof.

For closing the device for the purposes of packaging or transport, the same band 16 will be used, as can be seen in FIG. 3, in which the device assumes a substantially flattened structure.

With the device which is the subject of the present invention, it is possible to effect, easily and rapidly, the obstruction by constriction of the urinary duct in order to achieve an effective function of control of incontinence, the said device also being very easy to remove and not affected by being used from the left or the right, that is to say, independently of whether the user is right-handed or left-handed.

I claim:

1. A device for the control of masculine incontinence comprising:
   a laminar body including a layer of spongy material covered by a sheet of semi-rigid material;
   said body having first and second curved areas separated by a hinge fold, each of said curved areas being curved around an axis substantially parallel to said hinge;
   said first and second curved areas ending in respective first and second flat flanges capable of coinciding when the device is folded along said hinge;
   said first curved area having two closure points extending from the semi-rigid covering element and into the spongy layer along a line substantially parallel with said hinge, thereby giving rise to individual smoothly convex areas in the spongy layer for producing two successive interruptions of the urinary duct.

2. A device for the control of masculine incontinence as recited in claim 1, wherein, when the device is closed, the hinge fold is substantially U-shaped with short limbs.

3. A device for the control of masculine incontinence as recited in claim 2, wherein said hinge further comprises an axially aligned groove for providing greater flexibility.

4. A device for the control of masculine incontinence as recited in claim 1, further comprising:

a fastening area positioned on one of said first and second curved areas opposite said spongy layer, said fastening area being firmly matable to a closure tape suitable for wrapping the periphery of the device and retaining the device in the closed position.

5. A device for the control of masculine incontinence as recited in claim 4, wherein said fastening area comprises a plurality of hooks matable to loops on said closure tape.

6. A device for the control of masculine incontinence as recited in claim 1, wherein said closure points comprise indentations in the semi-rigid covering element.

* * * * *